United States Patent [19]

Schehlmann et al.

[11] Patent Number: 6,132,705

[45] Date of Patent: *Oct. 17, 2000

[54] COSMETIC OR PHARMACEUTICAL COMPOSITIONS FOR USE ON THE SKIN

[75] Inventors: Volker Schehlmann, Römerberg; Christian Schade, Ludwigshafen; Axel Sanner, Frankenthal; Karin Sperling, Neustadt; Hans-Ulrich Wekel, Ellerstadt, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/882,733

[22] Filed: Jun. 26, 1997

[30] Foreign Application Priority Data

Jul. 5, 1996 [DE] Germany .................. 196 272 04

[51] Int. Cl.⁷ .................................. A61K 31/215
[52] U.S. Cl. ......................... 424/78.02; 424/78.03; 424/78.06; 526/264; 526/303.1; 526/328.5; 526/329.2
[58] Field of Search ............... 526/279, 328.5, 526/329.2, 303.1, 264; 424/78.02, 78.03, 78.06

[56] References Cited

U.S. PATENT DOCUMENTS

| | | |
|---|---|---|
| 3,808,178 | 4/1974 | Gaylord . |
| 4,259,467 | 3/1981 | Keogh et al. . |
| 4,661,571 | 4/1987 | Kato et al. ............... 526/329.2 |
| 4,756,843 | 7/1988 | Jarrin et al. ............. 526/329.2 |
| 4,861,840 | 8/1989 | Lim et al. ................. 526/279 |
| 4,948,855 | 8/1990 | Novicky .................... 526/279 |
| 5,070,164 | 12/1991 | Min et al. ............... 526/329.2 |
| 5,219,560 | 6/1993 | Suzuki et al. .............. 526/279 |
| 5,276,070 | 1/1994 | Arroyo .................... 526/329.2 |
| 5,536,782 | 7/1996 | Takarada et al. ........... 526/279 |
| 5,700,585 | 12/1997 | Lee ....................... 526/328.5 |

FOREIGN PATENT DOCUMENTS

| | | | |
|---|---|---|---|
| 59-12907 | 1/1984 | Japan ................... 526/329.2 |
| 2-64117 | 3/1990 | Japan ................... 526/279 |
| 3-12416 | 1/1991 | Japan ................... 526/279 |
| 84/00969 | 3/1984 | WIPO .................... 526/279 |
| 86/01518 | 3/1986 | WIPO .................... 526/279 |

OTHER PUBLICATIONS

Ans 10 of 33 doc. 123:237539 in house computer searched pp. 21–24 Shinji et al. JP 07187951—950725.

*Primary Examiner*—Fred Zitomer
*Attorney, Agent, or Firm*—Keil & Weinkauf

[57] ABSTRACT

A cosmetic or pharmaceutical composition which comprises at least one polymer or copolymer which is obtainable by free-radical emulsion or suspension polymerization in the presence of at least one chain-transfer reagent, has a glass transition temperature above −35° C. and a content of organic volatile constituents ≦0.5% by weight, and is at least 20% by weight composed of a (meth)acrylic ester.

26 Claims, No Drawings

COSMETIC OR PHARMACEUTICAL COMPOSITIONS FOR USE ON THE SKIN

The present invention relates to cosmetic or pharmaceutical compositions for use on the skin, which comprise polymers or copolymers which are obtainable by free-radical emulsion or suspension polymerization in the presence of chain-transfer reagents to increase the water resistance.

Good water resistance is often desirable for cosmetic or pharmaceutical compositions applied to the skin. Compositions of these types are of particular interest when frequent contact of the skin with water or aqueous liquids, such as sweat, is observed, and an increased wet substantivity results in prolonged efficacy. In order to achieve the required water resistance, polymers are frequently added to compositions of these types. It should furthermore be noted that these compositions should neither dry out the skin nor lead to inflammations but, on the contrary, ideally have a moisturizing effect and be dispersible evenly on the skin.

DE-2 833 711 describes sun screen formulations which comprise oil-soluble acrylate polymers to increase the water resistance. Both homopolymers prepared from acrylic esters and copolymers of acrylic esters and carboxyl-containing monomers such as (meth)acrylic acid or itaconic acid are described. The polymers are prepared without chain-transfer reagents and, in particular, by solution polymerization in a cosmetically usable oil such as isopropyl palmitate and are formulated directly in the form of the resulting solution to give a sun screen composition.

Copolymers of N-vinylpyrrolidone and α-olefins and their use in cosmetic formulations are described, for example, in U.S. Pat. Nos. 5,219,559 and 3,423,381. They are prepared by solution polymerization without use of a chain-transfer agent and are further processed after removal of the solvent.

Although these prior art compositions have increased water resistance, they have various disadvantages which are attributable in particular to the processes used therein for preparing the polymers described. For example, there is frequently observed to be a high content of residual monomers and other odoriferous impurities which should be avoided in pharmaceutical and cosmetic compositions for toxicological and olfactory reasons. The necessary removal of these low molecular weight constituents is often possible only with great technical complexity or, in the case of solution polymerization, in fact technically impossible in practice.

Another disadvantage of these products is that the ease of handling is comparatively poor. In a solution polymerization, especially of acrylic esters, the polymer as results have an oily or waxy composition, which results in limitations on the choice of the subsequent pharmaceutical or cosmetic formulation and leads to relatively great technical complexity of processing for the manufacturer of such compositions.

It is an object of the present invention to provide acrylate-based cosmetic or pharmaceutical compositions with high water resistance, the intention being that the polymers present for this purpose be colorless, have little odor and be easy to handle.

We have found that this object is achieved by using (meth)acrylic ester polymers or their copolymers with monomers capable of free-radical copolymerization, which are obtainable by free-radical emulsion or suspension polymerization in the presence of chain-transfer reagents.

The present invention thus relates to a cosmetic or pharmaceutical composition which comprises at least one polymer or copolymer which is obtainable by free-radical emulsion or suspension polymerization in the presence of at least one chain-transfer reagent, has a glass transition temperature above $-35°$ C. (determined by DSC) and a content of organic volatile constituents $\leq 0.5\%$ by weight, and is at least 20% by weight composed of a (meth)acrylic ester.

Particularly suitable compositions are those comprising at least one polymer or copolymer composed of a) 40–100% by weight of at least one $C_1$–$C_{30}$ (meth)acrylic ester as monomer A, b) 0–30% by weight of at least one water-soluble monomer capable of free-radical copolymerization as monomer B, c) 0–40% by weight of at least one (meth)acrylamide which is capable of free-radical copolymerization and is unsubstituted or N-substituted by $C_1$–$C_{18}$-alkyl or -hydroxyalkyl as monomer C and d) 0–30% by weight of at least one monomer capable of free-radical copolymerization as monomer D.

If monomers B, C and D are present, their content is preferably at least 1% by weight.

The (meth)acrylic esters (monomers A) used in the composition of the polymers according to the invention are preferably esters of (meth)acrylic acid with $C_1$–$C_{30}$-alkyl alcohols, for example methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, t-butyl acrylate, t-butyl methacrylate, pentyl acrylate, pentyl methacrylate, n-hexyl acrylate, n-hexyl methacrylate, n-heptyl acrylate, n-heptyl methacrylate, n-octyl acrylate, n-octyl methacrylate, 2-ethylhexyl acrylate, 2-ethylhexyl methacrylate, decyl acrylate, decyl methacrylate, lauryl acrylate, lauryl methacrylate, palmityl acrylate, palmityl methacrylate, stearyl acrylate, stearyl methacrylate, hydrenol (meth)acrylate, behenyl (meth)acrylate, polyisobutene (meth)acrylate, phenoxyethyl acrylate or phenoxyethyl methacrylate, or $C_5$–$C_6$-cycloalkyl (meth)acrylates, it being possible for the cycloalkyl radical to be substituted by 1, 2 or 3 $C_1$–$C_4$-alkyl groups, for example cyclohexyl acrylate, cyclohexyl methacrylate, 4-methylcyclohexyl acrylate or 4-methylcyclohexyl methacrylate.

$C_2$–$C_6$ (meth)acrylic esters and $C_{12}$–$C_{22}$ (meth)acrylic esters are preferred.

Particularly preferred as monomer A are t-butyl acrylate, t-butyl methacrylate, isobutyl acrylate, isobutyl methacrylate and t-butyl acrylate or t-butyl methacrylate.

It is also possible to use in the composition of the polymers according to the invention water-soluble monomers which are capable of free-radical polymerization (monomers B) and which influence the physicochemical properties, such as the glass transition temperature and solubility, of the resulting copolymer, and the substantivity of a composition containing these polymers on the skin. They may also improve the compatibility with other components of the cosmetic or pharmaceutical preparation. Use of these monomers B in the composition of the copolymers according to the invention may furthermore optimize the sensation on the skin after use of the composition.

Preferred cosmetic or pharmaceutical compositions are therefore those comprising copolymers composed of at least one monomer A and at least one monomer B.

Monomers B which are suitable according to the invention comprise monoethylenically unsaturated $C_3$–$C_5$ carboxylic acids such as acrylic acid, methacrylic acid, crotonic acid, itaconic acid, maleic acid, fumaric acid, N-vinylsubstituted lactams, eg. N-vinylpyrrolidone, N-vinylvalerolactam and N-vinylcaprolactam, and hydroxyl-containing $C_2$–$C_6$ (meth)acrylic esters, such as hydroxyethyl (meth)acrylate.

The properties of the copolymers which are obtained in this way and are composed of monomers A and B can be further improved by including another monomer (monomer C) which can entirely or partly replace monomer B depending on the purpose of use.

Suitable and preferred as monomer C are (meth) acrylamides which are unsubstituted or N-substituted by $C_1$–$C_8$-alkyl or -hydroxyalkyl, such as acrylamide, methacrylamide, N-methylacrylamide, N-methylmethacrylamide, N-ethylacrylamide, N-ethylmethacrylamide N-propylacrylamide, N-propylmethacrylamide, N-isopropylacrylamide, N-isopropylmethacrylamide, N-n-butylacrylamide, N-n-butylmethacrylamide, N-isobutylacrylamide, N-isobutylmethacrylamide, N-t-butylacrylamide, N-t-butylmethacrylamide, N-pentylmethacrylamide, N-hexylacrylamide, N-hexylmethacrylamide, N-heptylacrylamide, N-heptylmethacrylamide, N-octylacrylamide, N-octylmethacrylamide, N-2-ethylhexylacrylamide, N-2-ethylhexylmethacrylamide, N-nonylacrylamide, N-nonylmethacrylamide, N-decylacrylamide, N-decylmethacrylamide, N-laurylacrylamide, N-laurylmethacrylamide, N-palmitylacrylamide, N-palmitylmethacrylamide, stearylacrylamide, N-stearylmethacrylamide, N-hydroxyethylacrylamide, N-hydroxyethylmethacrylamide, N-hydroxypropylacrylamide and N-hydroxypropylmethacrylamide. $C_4$–$C_{18}$-alkyl-substituted (meth)acrylamides are preferred, in particular N-t-butyl (meth)acrylamide.

Finally, it is possible for copolymers which are suitable according to the invention to contain units of another monomer (monomer D). In this case, monomers D can be copolymerized with monomers A alone or in combination with monomers B and/or C, depending on the purpose of use, for the composition of the polymers according to the invention.

Monomers D which are preferred according to the invention are $C_1$–$C_{30}$ vinyl esters, such as vinyl acetate, vinyl propionate, vinyl butyrate, vinyl valerate, vinyl 2-ethylhexanoate, vinyl decanoate, vinyl palmitate, vinyl stearate and vinyl laurate, $C_1$–$C_{30}$ vinyl ethers, such as methyl vinyl ether, ethyl vinyl ether, n-propyl vinyl ether, isopropyl vinyl ether, n-butyl vinyl ether, isobutyl vinyl ether, 2-ethylhexyl vinyl ether, decyl vinyl ether, dodecyl vinyl ether, stearyl vinyl ether, 2-(diethylamino)ethyl vinyl ether, 2-(di-n-butylamino)ethyl vinyl ether and methyldiglycol vinyl ether, vinylaromatic compounds, eg. styrene and substituted styrenes, such as p-methylstyrene and α-methylstyrene, and Si-containing monomers, in particular unsaturated polysiloxanes.

Preferred monomers D are vinyl esters, in particular $C_{12}$–$C_{22}$ vinyl esters, $C_{12}$–$C_{22}$ vinyl ethers, styrene and unsaturated polysiloxanes of the formula I:

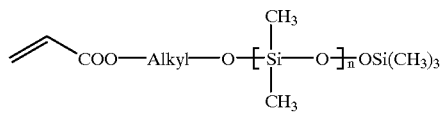

in which n is 6–50 and alkyl is a straight-chain or branched $C_2$–$C_{18}$-alkylene radical.

The physicochemical properties of the polymers or copolymers according to the invention depend on the nature of the monomers used, the relative amounts thereof and the polymerization conditions and can be specifically influenced by the choice of suitable parameters.

The polymers according to the invention have a glass transition temperature Tg above −35° C. The glass transition temperature is preferably ≧0° C., and particularly preferred polymers or copolymers have a glass transition temperature above 35° C. Polymers according to the invention with low glass transition temperatures are preferably prepared by emulsion polymerization, whereas polymers with higher glass transition temperatures are preferably obtainable by suspension polymerization. The upper limit of the glass transition temperature is generally 120° C. Very particularly preferred polymers or copolymers have a glass transition temperature in the range from 35° C. to 100° C.

The polymers generally have K values (method of H. Fickentscher, Cellulose-Chemie 13 (1932), 58–64 and 71–74) of >15, preferably >20. Polymers with a K value in the range from 20 to 60 are particularly preferred.

Polymerization of the monomers described above takes place by emulsion or suspension polymerization in an aqueous medium, preferably in water. Aqueous media also mean in this connection mixtures of water and water-miscible solvents such as methanol, ethanol, isopropanol etc.

The polymerization normally takes place with exclusion of oxygen at, for example, 30–100° C., preferably 50–95° C. The emulsion polymerization can be carried batchwise or continuously, whereas the suspension polymerization is usually carried out batchwise.

The polymerization according to the invention is of the free-radical type. Suitable polymerization initiators are the compounds which are normally used in free-radical polymerizations and which provide free radicals under the polymerization conditions, eg. peroxides, hydroperoxides, peroxodisulfate, percarbonate, peroxy esters, hydrogen peroxide and azo compounds. Examples of initiators are hydrogen peroxide, dibenzoyl peroxide, dicyclohexyl peroxydicarbonate, dilauroyl peroxide, methyl ethyl ketone peroxide, acetylacetone peroxide, t-butyl hydroperoxide, cumene hydroperoxide, t-butyl perneodecanoate, t-amyl perpivalate, t-butyl perpivalate, t-butyl perneohexanoate, t-butyl per-2-ethylhexanoate, t-butyl perbenzoate, lithium, sodium, potassium and ammonium peroxodisulfates, azoisobutyronitrile, 2,2'-azobis(2-amidinopropane) dihydrochloride, 2-(carbamoylazo)isobutyronitrile and 4,4'-azobis(4-cyanovaleric acid). Photoinitiators can also be used. The initiators are normally employed in amounts of up to 10, preferably 0.02 to 5, % of the weight of the monomers to be polymerized.

The initiators can be used alone or mixed with one another. It is also suitable to use known redox catalysts, in which case the reducing component is, as a rule, used in less than the stoichiometric amount. Also suitable as redox catalysts are reducing compounds such as ascorbic acid, alkali metal or ammonium sulfites, bisulfites, thiosulfates, dithionites and tetrathionates or phosphorus compounds which have a reducing action in which phosphorus has an oxidation number of from 1 to 4, for example sodium hypophosphite, phosphorous acid and phosphites.

In order to control the molecular weight of the polymers, the polymerization is carried out in the presence of chain-transfer reagents. Examples of suitable chain-transfer reagents are aldehydes, such as acetaldehyde, propionaldehyde, n-butyraldehyde and isobutyraldehyde, formic acid, ammonium formate, hydroxylammonium sulfate and hydroxylammonium phosphate. It is furthermore possible to employ chain-transfer reagents which contain sulfur in organically bound form, such as SH-containing organic compounds, such as thiomalic acid, thioglycolic acid, ethylhexyl thioglycolate, mercaptoacetic acid, mercaptopropionic acid, mercaptoethanol, mercaptopropanol, mercaptobutanol, mercaptohexanol, dodecyl mercaptan and T-dodecyl mercaptan. It is furthermore possible to use halogenated hydrocarbons as regulators, such as bromotrichloromethane and tetrachloromethane. Ethylhexyl thioglycolate and mercaptoethanol are preferred. The amount of chain-transfer reagent is 0.1–10, preferably 0.1–5, % of the weight of monomer.

The polymerization can be carried out in the presence of an emulsifier and/or protective colloid customary for these purposes. Examples of suitable protective colloids are polyvinyl alcohols, cellulose derivatives or polyvinylpyrrolidones. The emulsifiers may be anionic, cationic or nonionic in nature. Examples of suitable emulsifiers are ethoxylated mono-, di- and trialkylphenols (EO degree 3–50, alkyl radical: $C_4$–$C_9$), ethoxylated fatty alcohols (EO degree: 3–50, alkyl radical $C_8$–$C_{36}$), ethoxylated sorbitan esters, and alkali metal and ammonium salts of alkyl-sulfates (alkyl radical: $C_8$ to $C_{12}$), of sulfuric monoesters of ethoxylated alkanols (EO degree 4–30, alkyl radical $C_{12}$ to $C_{18}$) and ethoxylated alkylphenols (EO degree: 3–50, alkyl radical $C_4$ to $C_9$), of alkylsulfonic acids (alkyl radical: $C_{12}$ to $C_{18}$), of ligninsulfonic acid and of alkylarylsulfonic acids (alkyl radical: $C_9$ to $C_{18}$). Particularly suitable emulsifiers have proven to be the alkyldiphenyloxysulfonates.

The dispersions obtained by emulsion polymerization can be efficiently freed of residual monomers and other low molecular weight odorous substances which are unwanted for toxicological and olfactory reasons by passing in steam or nitrogen. These dispersions can be employed directly in the appropriate cosmetic or pharmaceutical compositions, in particular creams or lotions. The emulsion copolymers can, if the glass transition temperature of the polymer is sufficiently high, also be converted without difficulty by spray- or freeze-drying or else by coagulation and subsequent drying into powders which can be processed and handled very easily. These process steps make a further contribution to minimizing the content of low molecular weight volatile constituents.

The suspension polymers can likewise easily be extracted with water or steam and are also distinguished by excellent handling characteristics. The free-flowing powders can be formulated in accordance with requirements together with various cosmetic or pharmaceutical ancillary substances, in particular oils.

The emulsion or suspension polymers obtained in this way have an extremely low content of volatile organic constituents not exceeding 0.5% by weight. The polymers are colorless, virtually odorless and substantially oil-soluble.

The polymers or copolymers described above confer increased wet substantivity on the compositions according to the invention. The compositions preferably comprise 0.2–20, in particular 0.5–10, % by weight of polymer, based on the total weight of the composition.

A cosmetic or pharmaceutical composition of these types can be, for example, in the form of an oil, emulsion, eg. cream, lotion or milk, gel, pomade or spray. The composition and the processes for formulating these various application forms are known to the skilled worker.

Examples of suitable oily bases for the compositions according to the invention are the following oils or mixtures thereof: vegetable oils, such as sweet almond oil, avocado oil, castor oil, olive oil, grapeseed oil, clove oil, colza oil, arachis oil, corn oil, hazelnut oil, jojoba oil, safflower oil or wheatgerm oil, hydrocarbon oils such as liquid paraffin, Purcellin oil, perhydrosqualene and solutions of microcrystalline waxes in these oils, mineral oils or silicone oils. It is also possible to use other synthetic products such as esters, especially isopropyl palmitate, isopropyl myristate, butyl myristate, cetyl myristate, hexadecyl stearate, ethyl palmitate, and triglycerides of octanoic and decanoic acids and cetyl ricinoleate.

The compositions according to the invention may also contain certain waxes, in particular, carnauba wax, beeswax, ozokerite or candelilla wax.

Suitable emulsifiers in the composition of the emulsion according to the invention are conventional anionic, cationic, amphoteric and nonionic emulsifiers.

The compositions may furthermore contain conventional additives such as preservatives, antioxidants, perfumes, dyes, pigments, humectants, bulking agents such as talc, nylon, silk, starch or polyethylene powder, thickeners, stabilizers, buffers, spreading agents, acids, bases, in particular amines for partial or complete neutralization of carboxyl groups, sunscreen filters and pharmaceutical active substances such as liporegulators, antiinflammatory agents, antibiotics, keratolytic agents, vitamins, astringents, antifungal agents, insect repellants or vasoconstrictors.

The cosmetic and pharmaceutical compositions according to the invention are thus used, for example, in sunscreen preparations, face-, body- or hand-care compositions, insect-repellant compositions, lipsticks, make-up, eye shadows, mascaras, baby creams, preparations to protect the skin in incontinence, creams to protect against contact with chemicals or pesticides, or other pharmaceutical preparations for application to the skin.

The following examples illustrate the invention without restricting it.

The following abbreviations apply hereinafter:

| | |
|---|---|
| EA | ethyl acrylate |
| BA | butyl acrylate |
| EHA | 2-ethylhexyl acrylate |
| LA | lauryl acrylate (C12–C14-alcohol acrylic ester) |
| StA | stearyl acrylate |
| StMA | stearyl methacrylate |
| tBA | t-butyl acrylate |
| tBMA | t-butyl methacrylate |
| iBMA | isobutyl methacrylate |
| MMA | methyl methacrylate |
| VP | vinylpyrrolidone |
| AS | acrylic acid |
| MAS | methacrylic acid |
| NTBAM | N-t-butyl acrylamide |
| HEMA | hydroxyethyl methacrylate |
| AA | acrylamide |
| MAA | methacrylamide |
| BTCM | bromotrichloromethane |
| EHTG | ethylhexyl thioglycolate |
| ME | mercaptoethanol |
| S | styrene |

1. Preparation of Copolymers According to the Invention

Process 1: Emulsion Polymerization 450 g of the monomer mixture to be polymerized, the chain-transfer reagent and 1.1 g of initiator are added over the course of 2 hours to a stirred solution of 3.9 g of a suitable emulsifier or of an emulsifier mixture in 850 g of water at about 80° C. After the addition is complete, the mixture is stirred at about 80° C. for about 1.5 hours and, if necessary to reduce residual monomers, polymerization is completed by adding a redox system. Subsequently, steam is passed in until the content of steam-volatile components has fallen to the desired level. The dispersion is then converted into a powder in a known manner by spray-drying or freeze-drying or coagulation. Polymers are prepared by this process using the monomers and chain-transfer reagents indicated in the following table:

TABLE 1

| Example | Monomers | Monomer ratio | Chain-transfer reagent (based on monomer) | $T_g$ [° C.] |
|---|---|---|---|---|
| 1 | tBMA/EA | 90/10 | 0.6% BTCM | 85 |
| 2 | tBMA/EHA | 80/20 | 1.4% EHTG | 61 |
| 3 | tBA/EHA | 90/10 | 0.8% EHTG | 39 |
| 4 | iBMA/BA | 85/15 | 1.0% BTCM | 41 |
| 5 | tBMA/NTBAM/EA | 80/10/10 | 1.2% EHTG | 81 |
| 6 | tBMA/MMA/EHA | 80/10/10 | 1.5% EHTG | 78 |
| 7 | tBMA/EHA/MAS | 80/17/3 | 1.3% EHTG | 62 |
| 8 | tBMA/EHA/AS | 80/18/2 | 1.2% EHTG | 62 |
| 9 | tBMA/EHA/HEMA | 80/10/10 | 1.5% EHTG | 66 |
| 10 | tBMA/EHA/AA | 80/17/3 | 1.3% EHTG | 67 |
| 11 | tBMA/EHA/MAA | 85/15/5 | 1.0% EHTG | 68 |
| 12 | tBMA/EHA/MAS | 70/10/20 | 1.0% EHTG | 81 |
| 13 | tBMA/EA/MAS | 60/20/20 | 0.5% EHTG | 80 |
| 14 | tBA/EA/MAS | 55/20/25 | 0.8% EHTG | 65 |
| 15 | tBA/NTBAM/MAS | 40/30/30 | 0.3% BTCM | 76 |
| 16 | tBA/EHA/VP | 80/17/3 | 0.9% EHTG | 25 |

Process 2: Suspension Polymerization 135 g of the monomer mixture to be polymerized and the chain-transfer reagent are added to a stirred solution of 0.9 g of polyvinylpyrrolidone, $M_W$ about $(1.0–1.5) \times 10^6$ and 375 g of water. The mixture is heated to 80° C., and the first portion of the initiator, 0.5 g of t-butyl per-2-ethylhexanoate, is added. The mixture is then stirred at 80° C. for about 3.5 hours, and a further 0.5 g of initiator is added and stirred for 3.5 hours. To remove residual monomers, steam is passed into the suspension until the content of steam-volatile components has fallen to the desired level. After cooling, the polymer is filtered off and dried. Polymers are prepared by this process using the monomers and chain-transfer reagents indicated in the following Table 2:

TABLE 2

| Example | Monomers | Monomer ratio | Chain-transfer reagent | $T_g$ [° C.] |
|---|---|---|---|---|
| 17 | tBMA/LA | 90/10 | 1.0% ME | 80 |
| 18 | tBMA/StA | 70/30 | 1.5% ME | 72 |
| 19 | tBMA/EHA | 80/20 | 1.2% ME | 60 |
| 20 | tBMA/HEMA | 95/5 | 1.0% ME | 102 |
| 21 | tBMA/VP | 95/5 | 0.5% ME | 103 |
| 22 | iBMA/StMA | 70/30 | 1.5% ME | 38 |
| 23 | tBA/EHA/AS | 80/18/2 | 1.2% ME | 30 |
| 24 | tBMA/LA/S | 80/10/10 | 1.0% ME | 82 |

All the polymers indicated in the examples have a Gardner color number $\leq 2$ as 10% strength solution in THF, contain less than 0.5% of volatile organic constituents and are virtually odorless.

FORMULATION EXAMPLES

Example 25

Sunscreen cream with insect protection

| | Parts by weight. |
|---|---|
| Ceteareth-6 (and) stearyl alcohol | 1.00 |
| Ceteareth-25 | 1.00 |
| Glyceryl stearate SE | 6.00 |
| Cetearyl alcohol | 0.50 |
| Isopropyl palmitate | 6.00 |
| Octyl methoxycinnamate | 3.00 |
| Dimethyl phthalate | 5.00 |
| Benzophenone-3 | 2.00 |
| Polymer of Example 9 | 5.00 |
| Carbomer | 0.30 |
| Disodium-EDTA | 0.05 |
| Propylene glycol | 6.00 |
| Preservative | q.s. |
| Water | 60.60 |
| Tetrahydroxypropylethylenediamine | 0.55 |
| PEG-25 p-aminobenzoic acid | 3.00 |
| Perfume oil | q.s. |

Example 26

Sunscreen milk, W/O type

| | Parts by weight |
|---|---|
| PEG-7 hydrogenated castor oil | 6.00 |
| PEG-40 hydrogenated castor oil | 0.50 |
| PEG-45/dodecyl glycol copolymer | 2.00 |
| Isopropyl myristate | 8.00 |
| Liquid paraffin, high viscosity | 5.00 |
| Jojoba oil | 6.00 |
| Octyl methoxycinnamate | 7.00 |
| Benzophenone-3 | 2.00 |
| Magnesium stearate | 0.80 |
| Polymer of Example 7 | 2.00 |
| Preservative | q.s. |
| Magnesium sulfate.7H$_2$O | 0.50 |
| Glycerol 87% pure | 5.00 |
| Disodium EDTA | 0.10 |
| PEG-25 p-aminobenzoic acid | 5.00 |
| Water | 50.1 |
| Perfume oil | q.s. |

Example 27

Sunscreen lotion, O/W type

| | Parts by weight |
|---|---|
| Ceteareth-6 (and) stearyl alcohol | 1.50 |
| Ceteareth-25 | 3.00 |
| Cetearyl octanoate | 3.00 |
| Glyceryl stearate | 1.00 |
| Cetearyl alcohol | 3.00 |
| Dimethicone | 0.50 |
| Octyl salicylate | 5.00 |
| Benzophenone-3 | 6.00 |
| Octocrylene | 10.00 |
| Polymer of Example 7 | 2.00 |
| 1,2-Propylene glycol | 5.00 |
| Preservative | q.s. |
| Carbomer | 0.25 |
| Disodium EDTA | 0.20 |
| Water | 59.20 |
| Tetrahydroxypropylethylenediamine | 0.35 |
| Perfume oil | q.s. |

Example 28

Baby cream

| | Parts by weight |
|---|---|
| PEG-7 hydrogenated castor oil | 6.00 |
| Petrolatum | 10.00 |
| Beeswax | 2.00 |
| Eucerinum anhydricum | 1.00 |
| Microcrystalline wax | 2.00 |
| Aluminum stearate | 0.50 |
| Magnesium stearate | 0.50 |
| Cetearyl octanoate | 8.00 |
| (−)-α-Bisabolol nat. | 0.20 |
| Polymer of Example 11 | 10.00 |
| D-Panthenol USP | 8.00 |
| 1,2-Propylene glycol USP | 3.00 |
| Zinc oxide | 10.00 |
| Preservative | q.s. |
| Distilled water | 38.8 |
| Perfume oil | q.s. |

Example 29

Body milk, O/W type

| | Parts by weight |
|---|---|
| Ceteareth-6 (and) stearyl alcohol | 1.50 |
| Ceteareth-25 | 1.50 |
| Glyceryl stearate | 3.00 |
| Cetyl alcohol | 0.20 |
| Cetearyl octanoate | 5.00 |
| Liquid paraffin, high viscosity | 5.00 |
| Lanolin | 2.50 |
| (−)-α-Bisabolol nat. | 0.10 |
| Polymer of Example 3 | 3.00 |
| 1,2-Propylene glycol USP | 3.00 |
| Panthenol | 2.00 |
| Carbomer | 0.15 |
| Preservative | q.s. |
| Water | 72.85 |
| Tetrahydroxypropylethylenediamine | 0.20 |
| Perfume oil | q.s. |

Example 30

Face pack

| | Parts by weight |
|---|---|
| Ceteareth-6 (and) stearyl alcohol | 3.00 |
| Ceteareth-25 | 1.50 |
| Cetearyl alcohol | 5.00 |
| Cetearyl octanoate | 6.00 |
| Liquid paraffin, high viscosity | 6.00 |
| (−)-α-Bisabolol nat. | 0.20 |
| Glycerol monostearate | 3.00 |
| Polymer of Example 8 | 8.00 |
| 1,2-Propylene glycol USP | 2.00 |
| D-Panthenol USP | 5.00 |
| Preservative | q.s. |
| Water | 59.8 |
| Perfume oil | q.s. |
| Tocopheryl acetate | 0.50 |

Example 31

Hand cream

| | Parts by weight |
|---|---|
| Ceteareth-6 (and) stearyl alcohol | 2.00 |
| Ceteareth-25 | 2.00 |
| Cetearyl octanoate | 4.00 |
| Cetearyl alcohol | 3.50 |
| Glyceryl stearate SE | 3.50 |
| Liquid paraffin, high viscosity | 10.00 |
| (−)-α-Bisabolol nat. | 0.50 |
| Polymer of Example 11 | 6.00 |
| Panthenol | 4.00 |
| 1,2-Propylene glycol USP | 3.00 |
| Preservative | q.s. |
| Water | 59.50 |
| Perfume oil | q.s. |
| Soybean extract | 2.00 |

Example 32

Make Up

| | Parts by weight |
|---|---|
| Glycerol monostearate | 1.80 |
| Cetyl alcohol | 1.80 |
| Ceteareth-6 (and) stearyl alcohol | 1.80 |
| Ceteareth-25 | 1.80 |
| Caprylic acid/capric acid triglyceride | 5.30 |
| Liquid paraffin, high viscosity | 5.30 |
| Polymer of Example 15 | 4.00 |
| 1,2-Propylene glycol | 4.40 |
| Water | 61.50 |
| Preservative | q.s. |
| Perfume oil | q.s. |
| Brown iron oxides | 1.80 |
| Titanium dioxide | 10.50 |

Example 33

Lip gloss

| | Parts by weight |
|---|---|
| Candelilla wax | 5.30 |
| Beeswax | 1.10 |
| Microcrystalline wax | 1.10 |
| Cetyl palmitate | 2.00 |
| Liquid paraffin, high viscosity | 3.30 |
| Castor oil (and) glyceryl ricinoleate (and) octyldodecanol (and) carnauba (and) candelilla wax | 2.40 |
| (−)-α-Bisabolol nat. | 0.20 |
| Cetearyl octanoate | 16.00 |
| Hydrogenated coconut glycerides | 2.00 |
| Tocopheryl acetate | 0.50 |
| Polymer of Example 2 | 7.00 |
| Castor oil DAB 8 | 54.30 |
| Sicomet azorubine lake E 122 | 0.80 |
| Mica (and) titanium dioxide | 4.00 |

Example 34

Lipstick

| | Parts by weight |
|---|---|
| Carnauba wax | 3.00 |
| Candelilla wax | 3.50 |
| Beeswax | 2.00 |
| Microcrystalline wax (Permulgin 4200) | 3.50 |
| Microcrystalline wax (Permulgin 3220) | 3.50 |
| Cetyl palmitate | 1.50 |
| Petrolatum | 5.50 |
| Lanolin wax | 3.50 |
| Lanolin | 2.00 |
| Cetearyl octanoate | 10.00 |
| (−)-α-Bisabolol nat. | 0.20 |
| D,L-α-Tocopherol | 0.50 |
| Vitamin E acetate | 2.00 |
| Hydrogenated coconut glycerides | 3.50 |
| Polymer of Example 5 | 0.50 |
| Castor oil DAB 8 | 48.30 |
| Yellow iron oxides | 0.10 |
| Pigment Red 57:1 | 0.10 |
| Pigment Red 63:1 | 0.60 |
| Iron oxide (Sicopearl copper 1000) | 3.10 |
| Flamenco Red | 3.10 |

Example 35

Mascara

| | Parts by weight |
|---|---|
| Carbomer | 0.50 |
| Water | 57.5 |
| PVP | 3.00 |
| Water | 15.80 |
| Ethanol | 12.00 |
| Polymer of Example 16 | 0.50 |
| Preservative | q.s. |
| Triethanolamine | 0.70 |
| Black iron oxides | 10.00 |

Example 36

Eyebrow pencil

| | Parts by weight |
|---|---|
| Hydrogenated coconut glycerides | 14.0 |
| Caprylic/capric/stearic acid triglycerides | 8.00 |
| Caprylic/capric acid triglycerides | 8.00 |
| Bis-diglyceryl caprylate/caprate/isostearate/hydroxystearate adipate | 3.00 |
| Hydrogenated palm oil | 2.00 |
| Beeswax | 3.00 |
| Polymer of Example 13 | 1.00 |
| Talc | 20.00 |
| Titanium dioxide, micronized | 18.00 |
| Zinc oxide | 18.00 |
| Black iron oxides | 5.00 |
| Perfume oil | q.s. |

Example 37

Eyeshadow

| | Parts by weight |
|---|---|
| Talc | 19.80 |
| Potato starch | 9.90 |
| Magnesium stearate | 5.10 |
| Binder | 15.80 |
| Iron oxides (Sicopearl Copper 1000) | 49.40 |
| Binder: | |
| Petrolatum | 20.00 |
| Cetearyl octanoate | 10.00 |
| Dimethicone | 5.00 |
| Microcrystalline wax | 5.00 |
| PEG-7 hydrogenated castor oil | 3.00 |
| Polyglyceryl 2-sesquiisostearate (and) beeswax (and) mineral oil (and) magnesium stearate (and) aluminum stearate | 5.00 |
| Polymer of Example 1 | 1.00 |
| Panthenol | 3.00 |
| Preservative | q.s. |
| Water | 48.00 |
| Perfume oil | q.s. |

What is claimed is:

1. A cosmetic or pharmaceutical composition having an increased water resistance, and being adapted for the treatment of skin, comprising, in addition to at least one conventional cosmetic or pharmaceutical ancillary substance, an effective amount of at least one polymer or copolymer composed of
    a) from 40 to 100% by weight of at least one $C_1$–$C_{30}$ (meth)acrylic ester as monomer A,
    b) from 0 to 30% by weight of at least one water soluble monomer capable of free-radical copolymerization as monomer B,
    c) from 0 to 40% by weight of at least one (meth) acrylamide which is capable of free-radical copolymerization and is unsubstituted or N-substituted by $C_1$–$C_{18}$-alkyl or hydroxyalkyl as monomer C, and
    d) from 0 to 30% by weight of at least one monomer capable of free-radical copolymerization selected from the group consisting of $C_1$–$C_{30}$ vinyl esters, $C_1$–$C_{30}$ vinyl ethers and vinyl aromatic compounds as monomer D,
which polymer or copolymer is obtainable by free-radical emulsion or suspension polymerization in the presence of at least one chain-transfer reagent, and where the polymer or copolymer has a glass transition temperature above −35° C. and a content of organic volatile constituents ≦0.5% by weight, as a wet substantivity increasing agent.

2. The composition defined in claim 1, wherein the amount of monomer B is 1–30% by weight.

3. The composition defined in claim 1, wherein the amount of monomer C is 1–40% by weight.

4. The composition defined in claim 1, wherein the amount of monomer D is 1–30% by weight.

5. The composition defined in claim 1, wherein monomer A is selected from the group consisting of t-butyl acrylate, t-butyl methacrylate, isobutyl acrylate or isobutyl methacrylate.

6. The composition defined in claim 1, wherein monomer B is selected from the group consisting of monoethylenically unsaturated $C_3$–$C_5$ carboxylic acids, N-vinylpyrrolidone, N-vinylvalerolactam, N-vinylcaprolactam and hydroxyl-containing $C_2$–$C_6$ (meth) acrylic esters.

7. The composition defined in claim 1, wherein monomer C is selected from the group consisting of (meth) acrylamides which are unsubstituted or N-substituted by $C_4$–$C_{18}$-alkyl.

8. The composition defined in claim 1, wherein the polymer or copolymer has a glass transition temperature >0° C.

9. The composition defined in claim 1, wherein the chain transfer reagent is selected from aldehydes, SH-containing organic compounds and halogenated hydrocarbons.

10. The composition defined in claim 1, wherein the amount of chain-transfer reagent is 0.1–10% of the weight of the monomer.

11. The composition defined in claim 1, wherein the polymer or copolymer is essentially free of low molecular weight impurities.

12. The composition defined in claim 1, which comprises 0.2–20% by weight, based on the total weight of the composition, of the polymer or copolymer.

13. The composition defined in claim 1, which is in the form of a cream, lotion, milk, oil or gel.

14. The composition defined in claim 1, wherein monomer B is acrylic acid, methacrylic acid or hydroxyethyl (meth)acrylate.

15. The composition defined in claim 1, wherein monomer C is N-t-butylacrylamide.

16. The composition defined in claim 1, wherein monomer D is selected from the group consisting of $C_{12}$–$C_{22}$ vinyl esters, $C_{12}$–$C_{22}$ vinyl ethers, styrene and substituted styrenes.

17. The composition defined in claim 1, wherein the polymer or copolymer has a glass transition temperature >35° C.

18. The composition defined in claim 1, wherein the amount of chain-transfer reagent is 0.1–5% of the weight of the monomer.

19. The composition defined in claim 12, which comprises 0.5–10% by weight, based on the total weight of the composition, of the polymer or copolymer.

20. The composition defined in claim 1, comprising an oil as at least one conventional cosmetic or pharmaceutical ancillary substance.

21. The composition defined in claim 1, which is in the form of a spray.

22. A cosmetic or pharmaceutical composition having an increased water resistance, and being adapted for the treatment of skin, comprising, in addition to at least one conventional cosmetic or pharmaceutical ancillary substance, an effective amount of at least one polymer or copolymer composed of a) from 40 to 100% by weight of at least one $C_2$–$C_6$ (meth)acrylic ester or $C_{12}$–$C_{22}$ (meth)acrylic ester as monomer A, b) from 0 to 30% by weight of at least one water soluble monomer capable of free-radical copolymerization as monomer B, c) from 0 to 40% by weight of at least one (meth) acrylamide which is capable of free-radical copolymerization and is unsubstituted or N-substituted by $C_1$–$C_{18}$-alkyl or hydroxyalkyl as monomer C, and d) from 0 to 30% by weight of at least one monomer capable of free-radical copolymerization selected from the group consisting of $C_1$–$C_{30}$ vinyl esters, $C_1$–$C_{30}$ vinyl ethers and vinyl aromatic compounds as monomer D, which polymer or copolymer is obtainable by free-radical emulsion or suspension polymerization in the presence of at least one chain-transfer reagent, and where the polymer or copolymer has a glass transition temperature above −35° C. and a content or organic volatile constituents $\leq 0.5\%$ by weight, as a wet substantivity increasing agent.

23. The composition defined in claim 22, wherein at least one of the monomers A is selected from the group consisting of ethyl acrylate, ethyl methacrylate, n-butyl acrylate, n-butyl methacrylate, isobutyl acrylate, isobutyl methacrylate, t-butyl acrylate, t-butyl methacrylate, 2-ethylhexyl acrylate, 2-ethylhexyl methacrylate, lauryl acrylate, lauryl methacrylate, stearyl acrylate and stearyl methacrylate.

24. The composition defined in claim 22, wherein the monomers A are selected from the group consisting of ethyl acrylate, ethyl methacrylate, n-butyl acrylate, n-butyl methacrylate, isobutyl acrylate, isobutyl methacrylate, t-butyl acrylate, t-butyl methacrylate, 2-ethylhexyl acrylate, 2-ethylhexyl methacrylate, lauryl acrylate, lauryl methacrylate, stearyl acrylate and stearyl methacrylate.

25. The composition defined in claim 22, wherein at least one of the monomers A is selected from the group consisting of t-butyl acrylate, t-butyl methacrylate, isobutyl acrylate or isobutyl methacrylate.

26. The composition defined in claim 22, wherein at least one of the monomers A is selected from the group consisting of t-butyl acrylate and t-butyl methacrylate.

* * * * *